(12) United States Patent
Neo et al.

(10) Patent No.: US 10,194,995 B2
(45) Date of Patent: Feb. 5, 2019

(54) SYSTEMS AND METHODS FOR EN BLOC REGISTRATION IN NAVIGATED SURGERY

(71) Applicant: Medos International Sarl, Le Locle (CH)

(72) Inventors: Masashi Neo, Kyoto (JP); J. Riley Hawkins, Cumberland, RI (US); Aniruddha Raina, Troy, MI (US)

(73) Assignee: Medos International Sarl, Le Locle (CH)

( * ) Notice: Subject to any disclaimer, the term of this patent is extended or adjusted under 35 U.S.C. 154(b) by 14 days.

(21) Appl. No.: 15/375,424

(22) Filed: Dec. 12, 2016

(65) Prior Publication Data

US 2018/0161075 A1 Jun. 14, 2018

(51) Int. Cl.
*A61B 17/70* (2006.01)
*A61B 17/88* (2006.01)
(Continued)

(52) U.S. Cl.
CPC .... *A61B 34/20* (2016.02); *A61B 2017/00991* (2013.01); *A61B 2034/2055* (2016.02);
(Continued)

(58) Field of Classification Search
CPC . A61B 34/20; A61B 17/7067; A61B 17/7094; A61B 2034/2055;
(Continued)

(56) References Cited

U.S. PATENT DOCUMENTS 5,658,286 A * 8/1997 Sava ............... A61B 17/7013
264/4
7,107,091 B2 9/2006 Jutras et al.
(Continued)

FOREIGN PATENT DOCUMENTS

EP 1836978 A1 9/2007
WO 00/21442 A1 4/2000

OTHER PUBLICATIONS

International Search Report and Written Opinion for Application No. PCT/US2017/062468, dated Mar. 7, 2018 (14 pages).

*Primary Examiner* — Pedro Philogene
*Assistant Examiner* — David C Comstock
(74) *Attorney, Agent, or Firm* — Nutter McClennen & Fish LLP

(57) ABSTRACT

Systems and methods for registering and tracking multiple anatomical structures, e.g., multiple vertebrae, as a single functional unit for surgical procedures are disclosed herein. In some embodiments, the system can include a bone bridge for attaching a navigation marker to multiple vertebrae and for limiting or preventing movement between the multiple vertebrae. Various ways of attaching the bone bridge are disclosed, including fasteners that extend through gaps or throughholes formed in the bridge, bridges having a jaw portion that clamps the underlying bone, and bridges formed of adhesive or cement and directly attached to the bone. Various adjustment features are also disclosed, including joints that allow the position and/or orientation of the bridge to be adjusted in one or more degrees of freedom, and bridges that include telescoping portions or other features for adjusting a length of the bridge.

19 Claims, 7 Drawing Sheets

(51) Int. Cl.
    *A61B 34/20*     (2016.01)
    *A61B 17/00*     (2006.01)
    *A61B 90/00*     (2016.01)

(52) U.S. Cl.
    CPC ............... *A61B 2090/3916* (2016.02); *A61B 2090/3983* (2016.02)

(58) Field of Classification Search
    CPC .... A61B 2090/3916; A61B 2090/3983; A61B 2017/00991
    USPC ....... 606/262, 256, 258, 259, 264, 277, 279; 600/414, 415, 417, 424–427, 429
    See application file for complete search history.

(56) References Cited

U.S. PATENT DOCUMENTS

| | | | | |
|---|---|---|---|---|
| 8,480,718 | B2 * | 7/2013 | Protopsaltis | A61B 17/7013 606/262 |
| 2002/0198526 | A1 * | 12/2002 | Shaolian | A61B 17/1671 606/254 |
| 2013/0090692 | A1 * | 4/2013 | Nuckley | A61B 17/7047 606/277 |
| 2016/0166335 | A1 * | 6/2016 | Roger | A61B 17/1703 606/130 |

* cited by examiner

SYSTEMS AND METHODS FOR EN BLOC REGISTRATION IN NAVIGATED SURGERY

FIELD

Systems and methods for registering and tracking multiple anatomical structures, e.g., multiple vertebrae, as a single functional unit during surgical procedures are disclosed herein.

BACKGROUND

There is often a need to track the location of anatomical structures during a surgical procedure. For example, in spinal surgery, the abundance of sensitive body tissues around the spine demands extreme precision to ensure that paralysis, and even death, is avoided. Surgical navigation systems are often used for such surgeries to provide approximate locations of vertebral levels and spinal segments to the surgeon, e.g., during insertion of pedicle or lateral mass screws. A typical surgical navigation system registers and tracks each vertebral level individually relative to both the patient and other vertebral levels by affixing navigation markers to each vertebra.

Existing surgical navigation systems can have numerous shortcomings. Instrumenting each individual vertebra with a navigation marker can further clutter an already limited surgical space and increase the complexity, cost, and processing requirements of the navigation system. Individual vertebrae can also shift or rotate relative to each other during the surgery, requiring frequent re-registration to ensure that the proper reference frame is maintained. Placing navigation markers on each vertebra can also be overly invasive and increase surgeon fatigue, as well as time spent in the operating room.

Accordingly, there is a continual need for systems and methods that improve registration and tracking of anatomical structures during surgical procedures.

SUMMARY

Systems and methods for registering and tracking multiple anatomical structures, e.g., multiple vertebrae, as a single functional unit for surgical procedures are disclosed herein. In some embodiments, the system can include a bone bridge for attaching a navigation marker to multiple vertebrae and for limiting or preventing movement between the multiple vertebrae. Various ways of attaching the bone bridge are disclosed, including fasteners that extend through gaps or throughholes formed in the bridge, bridges having a jaw portion that clamps the underlying bone, and bridges formed of adhesive or cement and directly attached to the bone. Various adjustment features are also disclosed, including joints that allow the position and/or orientation of the bridge to be adjusted in one or more degrees of freedom, and bridges that include telescoping portions or other features for adjusting a length of the bridge.

In some embodiments, a surgical navigation method includes attaching a plurality of vertebrae of a patient to one another using a bridge, the bridge limiting or preventing relative movement between the plurality of vertebrae, the plurality of vertebrae defining a single functional unit once connected to the bridge, the bridge having a navigation marker; and, using a surgical navigation system, guiding movement of a navigated object relative to a constituent member of the functional unit based on the navigation marker.

The navigation maker of the bridge and a navigation marker of the navigated object can be the only navigation markers used in guiding movement of the object. The navigated object can be or can include at least one of a bone anchor and a surgical instrument. Said movement can include driving the navigated object into the constituent member of the functional unit. The constituent member can be or can include one of the plurality of vertebrae to which the bridge is attached or a vertebra disposed between the plurality of vertebrae. The bridge can limit or prevent relative movement between the plurality of vertebrae and any vertebrae disposed between the plurality of vertebrae. The method can include determining a position and orientation of the navigated object relative to a constituent member of the functional unit. Attaching the plurality of vertebrae can include inserting a screw through an opening formed in the bridge and driving the screw into one of the plurality of vertebrae. Attaching the plurality of vertebrae can include clamping the plurality of vertebrae between first and second jaws of the bridge. Clamping the jaws can include tightening a screw within the bridge to move the jaws towards one another. Clamping the jaws can include squeezing the jaws together using at least one of a clamping tool and a bias force applied to the jaws. Attaching the plurality of vertebrae can include forming the bridge from a curable material in contact with the plurality of vertebrae. The method can include adjusting a length of the bridge based on a length of the functional unit. The method can include adjusting a position and/or orientation of the bridge relative to the plurality of vertebrae using one or more jointed arms of the bridge. Attaching the plurality of vertebrae can include attaching the spinous processes of the plurality of vertebrae to the bridge.

In some embodiments, a surgical navigation method includes attaching spinous processes of a plurality of vertebrae of a patient to one another using a bridge, the bridge immobilizing the plurality of vertebrae relative to one another and having a navigation marker attached thereto; and registering or tracking the plurality of vertebrae as a single functional unit using the navigation marker.

In some embodiments, a surgical device includes a bridge having a first end and a second end, the bridge having a length between the first and second ends sufficient to span multiple vertebrae of a patient; a securement device configured to attach the bridge to a plurality of vertebrae to connect and immobilize the vertebrae; and a navigation marker formed on or coupled to the bridge.

The device can include a surgical navigation system configured to track the plurality of a vertebrae as a single functional unit using the navigation marker. The bridge can include a continuous slot that extends substantially from the first end to the second end of the bridge. The securement device can include a plurality of screws inserted through the slot. The bridge can include a plurality of discrete openings. The securement device can include a plurality of screws inserted through the openings. The securement device can include first and second jaws configured to clamp onto a plurality of vertebrae. The securement device can include a screw configured to be tightened to force the first and second jaws towards one another. The securement device can include a curable material from which at least a portion of the bridge is formed. The securement device can include first and second arms extending from the bridge, the arms including at least one joint to allow adjustment of a position or orientation of the bridge. The length of the bridge can be adjustable. The length of the bridge can be adjustable by a telescoping portion of the bridge.

BRIEF DESCRIPTION OF THE DRAWINGS

The following detailed description is provided with the accompanying drawings, in which.

DETAILED DESCRIPTION

Systems and methods for registering and tracking multiple anatomical structures, e.g., multiple vertebrae, as a single functional unit for surgical procedures are disclosed herein. In some embodiments, the system can include a bone bridge for attaching a navigation marker to multiple vertebrae and for limiting or preventing movement between the multiple vertebrae. Various ways of attaching the bone bridge are disclosed, including fasteners that extend through gaps or throughholes formed in the bridge, bridges having a jaw portion that clamps the underlying bone, and bridges formed of adhesive or cement and directly attached to the bone. Various adjustment features are also disclosed, including joints that allow the position and/or orientation of the bridge to be adjusted in one or more degrees of freedom, and bridges that include telescoping portions or other features for adjusting a length of the bridge.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments.

Figure 1:
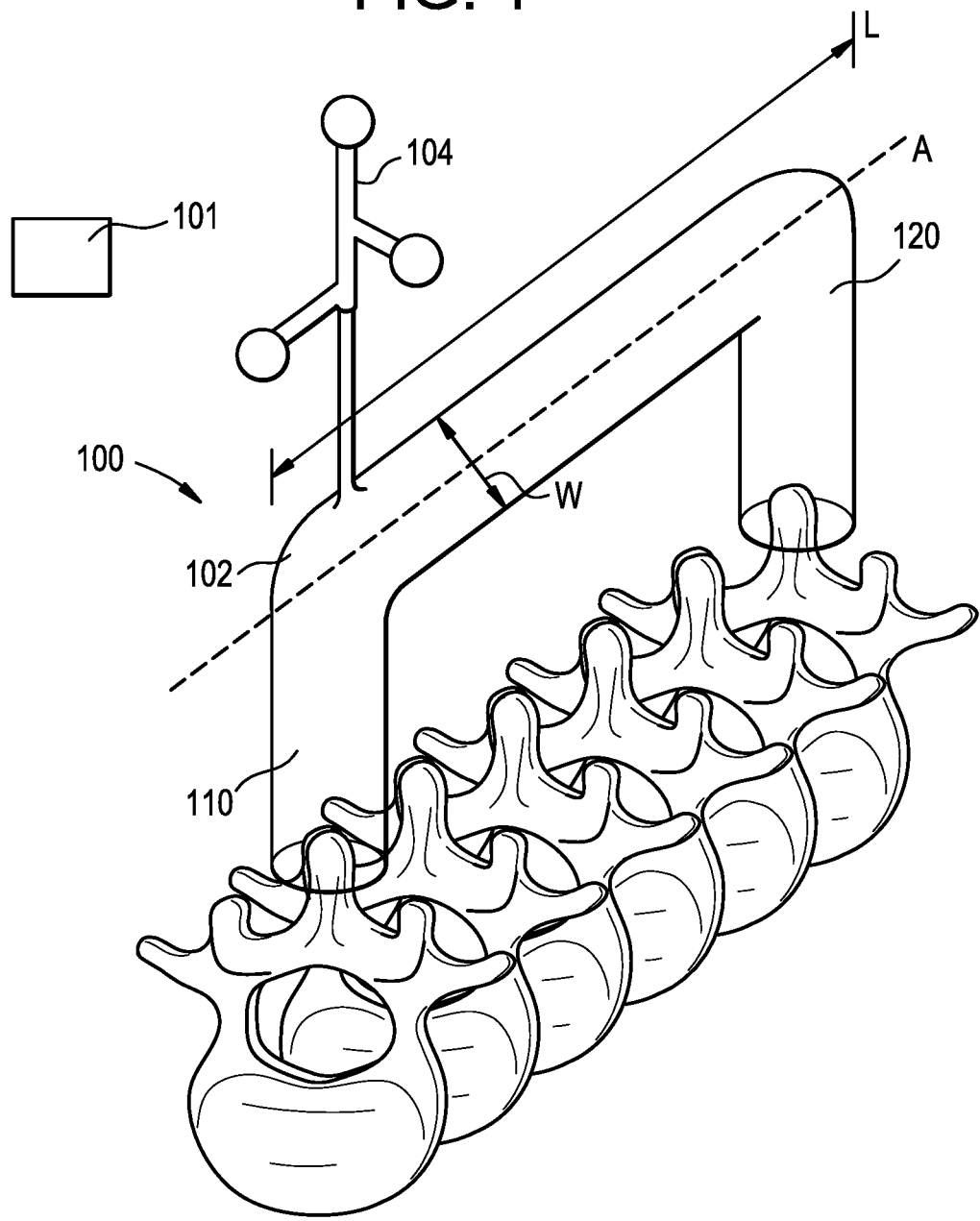
FIG. 1 is a perspective view of an en bloc registration and tracking system attached to a vertebral column.

FIG. 1 illustrates a system 100 which can be used, for example, to register and track multiple vertebral levels as a single functional unit for surgical procedures. As shown, the system 100 can include a bridge 102 and a navigation marker 104 configured to be attached to the patient. The system 100 can also include a navigation system 101 for registering and tracking the position and/or orientation of the marker 104 and, by extension, the bridge 102 and the anatomy to which the bridge is attached. The bridge 102 and the marker 104 can be a single monolithic unit, or can be separate components permanently or temporarily joined to one another. For example, the marker 104 can be welded or permanently affixed to the bridge 102 during manufacturing, or can be selectively coupled to the bridge via a mating interface such as a threaded, snap-fit, or interference-fit connection. The system 100 can provide a connection for multiple vertebral levels defining a spinal segment such that the spinal segment can be tracked by the navigation system 101 as a single functional unit. In use, the system 100 can be secured to multiple vertebral levels of a patient's spinal column, though it will be appreciated that the system 100 can be attached to other anatomical structures of the patient, including multiple bones, multiple bone fragments, long bones, non-bone structures, and so forth.

The bridge 102 can be secured to the patient to stabilize the vertebrae and to limit or prevent relative movement of the vertebrae, obviating the need for tracking vertebral levels individually as is typically required with existing methods in navigation assisted surgery. The bridge can be attached to each of a plurality of adjacent vertebrae, or can be attached to non-adjacent vertebrae having non-attached intermediate vertebrae therebetween. As shown in the illustrated embodiment, the bridge 102 skips four vertebral levels, though it will be appreciated that the bridge 102 can skip a fewer, or greater, number of vertebral levels. Forming a single functional unit with a bridge that skips vertebral levels can provide more access to the skipped levels and reduce the complexity or invasiveness of the surgery while still achieving sufficient navigation accuracy. The bridge 102 can have a low-profile geometry that can allow it to be attached in relatively small spaces or to provide sufficient clearance to complete the surgical procedure. This can allow the bridge 102 to be used with multiple vertebrae in the spinal column, even when the vertebrae are very closely-spaced, such as the cervical vertebrae or the vertebrae of pediatric or small patients.

The bridge 102 can be an elongate plate as shown, or can take other forms, such as a bone plate, rod, clamp, wire, tether, and the like. The bridge 102 can have a circular transverse cross-section or any of a variety of other cross-sections, such as oval, oblong, square, rectangular, triangular, hexagonal, and so forth. The bridge 102 can have a length L, a width W, and a central longitudinal axis A. In the illustrated embodiment, the bridge 102 is attached to the spinous processes of first and second vertebrae, though it will be appreciated that the bridge can be attached at various other locations or to other portions of the vertebrae, such as the superior processes, the articular processes, the transverse processes, the pedicles, the laminae, the vertebral body, and so forth. The bridge 102 can be attached to the skull, to the cervical, thoracic, lumbar, and/or sacral regions of the spine, to the hips, to the shoulders, or to any combination thereof. In an exemplary embodiment, the bridge can extend from C2 to C7 to define a functional unit. In another exemplary embodiment, the bridge can extend from C3 to C5. When implanted in a patient, the longitudinal axis A can extend parallel to the midline of the spinal column, though it will be appreciated that the bridge 102 can extend perpendicular to the midline or at an oblique angle with respect to the midline. While a single bridge is shown, multiple bridges 102 can be attached to the patient simultaneously to define multiple en bloc units.

The bridge 102 can be substantially straight along its length, or can include one or more bends or curves formed therein. The bridge 102 can be malleable or bendable such that it can be bent before or during a procedure to conform to the spine or to hold a spinal segment at a desired position.

The bridge 102 can be formed from any of a variety of materials suitable for use in surgical applications, including metals such as titanium, titanium alloys, or stainless steel, polymers such as PEEK, ceramics, fibers such as carbon fiber, and combinations thereof. As discussed below, the bridge 102 can also be formed from a curable material, such as a glue, adhesive, cement, composite, thermoplastic, fiberglass, hardenable sterile tape, etc. The curable material can be reinforced with a fabric or mesh.

The navigation marker 104 can be attached to the bridge 102 such that a position and orientation of the bridge with respect to the marker 104 is known. The marker 104 can be embedded in a surface of the bridge or can extend outward from the bridge as shown. The marker 104 can be located anywhere along the length L or the width W of the bridge 102.

While a single marker 104 is shown, the bridge 102 can include multiple markers, e.g., one at each end. Use of multiple markers 104 can improve tracking accuracy, field of view, or redundancy. The marker 104 can be detected by the navigation system 101, can communicate with the navigation system 101, or can be otherwise operably coupled to the navigation system 101 to allow the position and/or orientation of the bridge 102 and the underlying anatomy to be registered with and tracked by the navigation system 101. Having the bridge 102 connect the vertebrae as a single functional unit allows for tracking of the unit as a whole and can prevent the need to place a separate marker on each vertebra and conduct a cumbersome and time-consuming registration process for a large number of markers. The cost and complexity of the navigation system 101 can be reduced by reducing the number of markers that the system must track. Use of a single marker can also provide greater access to the vertebral column and a less cluttered surgical site.

It will be appreciated that the structure and operation of the marker 104 can vary depending on the type of navigation system 101 used. In the illustrated embodiment, the marker 104 includes three sphere-shaped fiducials for use with an optical navigation system. The fiducials can be arranged in predetermined positions and orientations with respect to one another. In the illustrated embodiment, three fiducials are aligned so as to lie in planes that are perpendicular to one another to set a Cartesian reference frame. The fiducials can be positioned within a field of view of the navigation system 101 and can be identified in images captured by the navigation system. Exemplary fiducials include infrared reflectors, LEDs, and so forth. The marker 104 can be or can include an inertial measurement unit (IMU), an accelerometer, a gyroscope, a magnetometer, other sensors, or combinations thereof. The sensors can transmit position and/or orientation information to the navigation system 101, e.g., to a processing unit of the navigation system.

The marker 104 can be configured to be visible or detectable in patient imaging performed preoperatively, intraoperatively, or postoperatively. For example, the marker 104 can include radiopaque portions to facilitate visualization of the marker in X-ray, CT, or fluoroscopy. By way of further example, the marker 104 can include metallic, magnetic, or other materials visible under MRI.

Any of a variety of surgical navigation systems 101 can be used, including commercially available systems such as those offered by BRAINLAB AG of Germany. The navigation system 101 can include an imaging system with a camera or image sensor that captures images of a surgical site and objects within the surgical site, such as the marker 104 and a similar marker attached to an instrument. The captured images can be registered to one or more patient images. The captured images and/or the patient images can be processed using a processor to determine a position and/or orientation of the instrument relative to an anatomy of the patient. This information can be communicated to a user, e.g., using an electronic display or a tactile, audible, or visual feedback mechanism.

The bridge 102 can be attached to the patient in various ways. For example, as shown in FIG. 1, the bridge 102 can include first and second arms 110, 120 for attaching the bridge 102 to the vertebral column. The arms 110, 120 of the bridge 102 can be anchored to individual vertebrae to form a single functional unit therebetween. Prior to attachment of the bridge 102, individual vertebral levels can be prone to movement and shifting in relation to one another. When the first and second arms 110, 120 are attached to the vertebral column, a spinal segment is defined therebetween. The bridge 102 can provide stability to the spinal segment to help minimize or eliminate relative motion between the constituent vertebrae of the segment, thereby minimizing or eliminating the need for re-registration. Once the spinal segment is formed, the vertebrae in the spinal segment, including the intermediate vertebrae, form an en bloc unit that can be tracked as a whole.

The arms 110, 120 can be attached to the patient in various ways, such as via screws, fasteners, nails, bone cement, glue, adhesive, hooks, clamps, and so forth. The arms 110, 120 can include one or more joints to allow the position and/or orientation of the bridge 102 to be adjusted relative to the patient in one or more degrees of freedom.

FIGS. 2-7 illustrate a number of variations on the system 100 described above. Except as indicated or as will be readily appreciated by one having ordinary skill in the art having read the present disclosure, the structure and operation of these variations is substantially the same as that of the system 100 described above and therefore a detailed description is omitted here for the sake of brevity.

Figure 2:
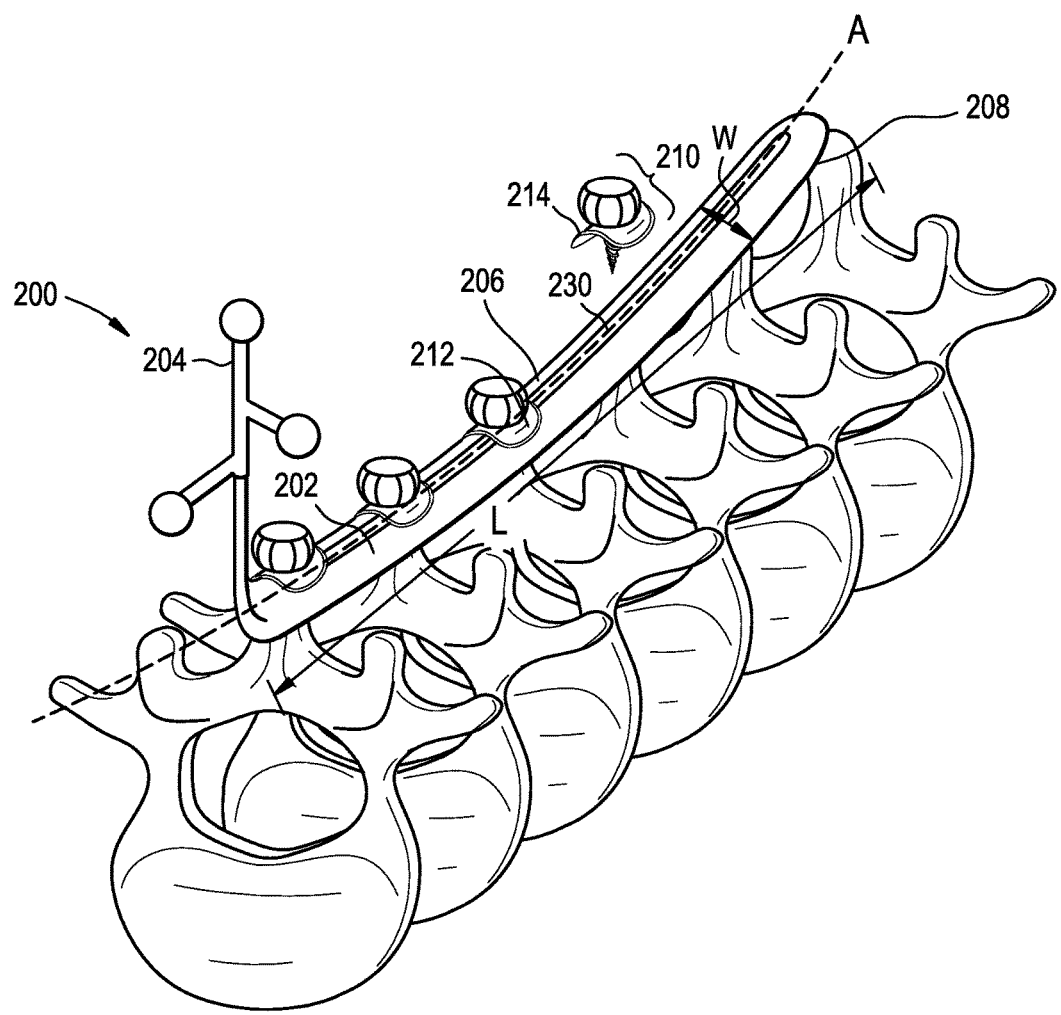
FIG. 2 is a perspective view of an en bloc registration and tracking system attached to a vertebral column, the system having a bridge with an elongate slot that extends through the bridge.

FIG. 2 illustrates a system 200 which can be used, for example, to register and track multiple vertebral levels as a single functional unit for surgical procedures.

As shown, the system 200 can include a bridge 202 configured for attachment to a patient's spine and a navigation marker 204 coupled to or formed integrally with the bridge. The bridge 202 can include an upper surface 206 and a lower bone-contacting surface 208, with an elongate slot 230 extending therebetween. The bridge can be configured to contact each of a plurality of vertebrae in a segment defined by the opposed ends of the plate as shown, though it will be appreciated that the bridge can be shaped so as not to contact one or more vertebrae in the segment. The elongate slot 230 can extend along substantially the entire length L of the upper and lower surfaces 206, 208 of the bridge 202, or along only a portion of the length L of the upper and lower surfaces. Similarly, the elongate slot 230 can extend along substantially the entire width W of the upper and lower surfaces 206, 208 of the bridge 202, or along only a portion of the width W of the upper and lower surfaces. In the illustrated embodiment, the bridge 202 includes only one slot 230 formed therein, though in other embodiments the bridge 202 can include multiple slots formed therein. In these embodiments, the multiple slots can be located in a staggered arrangement relative to one another along the upper and lower surfaces 206, 208 of the bridge 202. The slot 230 can be aligned along the central longitudinal axis A of the bridge 202, or located to either side of the axis A along the surfaces of the bridge 202.

The elongate slot 230 can be configured to receive one or more securement devices therethrough for attaching the bridge 202 to the vertebral column. For example, one or more screws 210 can be inserted through the elongate slot 230 to attach the system 200 to the patient. The illustrated slot 230 can allow screws 210 to be inserted at any location along the bridge 202, though it will be appreciated that the slot 230 can alternatively have designated positions through which the screws 210 can be inserted. The bridge 202 can provide flexibility to the user in selecting which vertebrae to attach to the bridge 202 and where on the vertebrae the screws 210 are inserted. The user can choose to secure the bridge 202 to every vertebral level, or to skip one or more vertebral levels.

The elongate slot 230 can support various types of securement devices therein. In the illustrated embodiment, finger screws attach the bridge 202 to the vertebral column, though it will be appreciated that other types of fasteners, e.g., pins, hooks, nails, bolts, wires, and the like can be used to attach the bridge 202 to the vertebral column. Use of finger screws can allow the surgeon to more easily and efficiently maneuver the screw for implantation into the vertebral column such that use of a separate tool for insertion is not required. Screws with a driving interface for engagement with a driver instrument can be used instead or in addition. The screws 210 can include a washer 212 rotatably coupled thereto or disposed thereon. The washer 212 can allow the screw 210 to be inserted at various angles relative to the bridge 202, can distribute screw forces over a broader area of the bridge 202, and/or can limit or prevent toggling between the screw 210 and the bridge 202. The washer 212 can include a concave surface 214 configured to abut a corresponding convex surface of the bridge 202.

Figure 3:
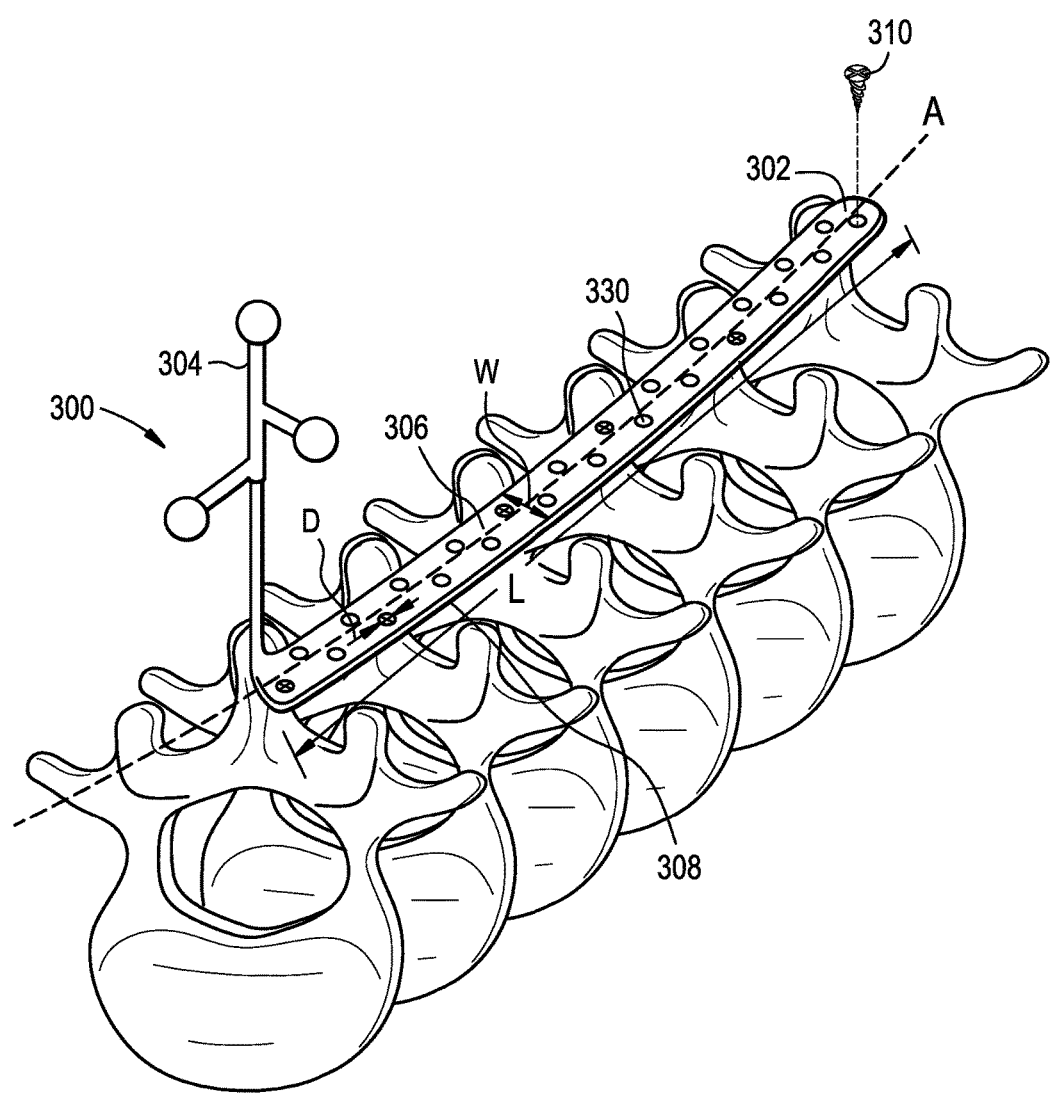
FIG. 3 is a perspective view of an en bloc registration and tracking system attached to a vertebral column, the system having a bridge with throughholes that extend through the bridge.

FIG. 3 illustrates a system 300 which can be used, for example, to register and track multiple vertebral levels as a single functional unit for surgical procedures.

As shown, the system 300 can include a bridge 302 configured for attachment to a patient's spine and a navigation marker 304 coupled to or formed integrally with the bridge. The bridge 302 can include an upper surface 306 and a lower surface 308, with one or more throughholes 330 extending therebetween. The throughholes 330 can allow for screws or other securement devices to be inserted through the bridge 302 at any of a plurality of discrete locations to attach the bridge to the patient. The throughholes 330 can be arranged along the upper and lower surfaces 306, 308 of the bridge. The throughholes 330 can be arranged in rows that extend along substantially the entire length L of the upper and lower surfaces 306, 308 of the bridge 302, or along only a portion of the length L of the upper and lower surfaces. Similarly, the throughholes 330 can extend along substantially the entire width W of the upper and lower surfaces 306, 308 of the bridge 302, or along only a portion of the width W of the upper and lower surfaces. Arranging a plurality of throughholes in rows can allow for multiple access points to a single vertebral level for a more secure attachment of the bridge 302 to the vertebral column and/or more flexibility in selecting screw locations.

The throughholes 330 can be located on the central longitudinal axis A of the bridge 302, or as shown can be arranged in rows that are offset from one or both sides of the central longitudinal axis A. The throughholes 330 can be staggered in relation to one another to maximize the number of holes per unit length of the bridge 302 for a given diameter hole.

Each throughhole 330 can receive a securement device therethrough for attaching the bridge 302 to the vertebral column. For example, one or more screws 310 can be inserted through the throughholes 330 to attach the bridge 302 to one or more vertebral levels. Each throughhole 330 can have a diameter D that is configured to support a screw 310 therethrough. It will be appreciated that the diameter D of each throughhole 330 can vary. The diameter D of each throughhole can be ½ of the width W of the bridge 302, ⅓ of the width W of the bridge 302, ¼ of the width W of the bridge 302, ⅕ of the width W of the bridge 302, ⅙ of the width W of the bridge 302, and so forth.

In the illustrated embodiment, the location of each throughhole 330 can designate a position through which a screw 310 can be inserted. It will be appreciated that while all of the throughholes 330 can have a screw 310 disposed therein, a smaller number of screws can be used such that a number of the throughholes remain unfilled, as in the illustrated embodiment. The number of screws 310 that can be used to secure the bridge to the vertebral column can thus vary. It will also be appreciated that the screws 310 can have additional features, such as locking features, washers, anti-backout features, etc.

Figure 4:
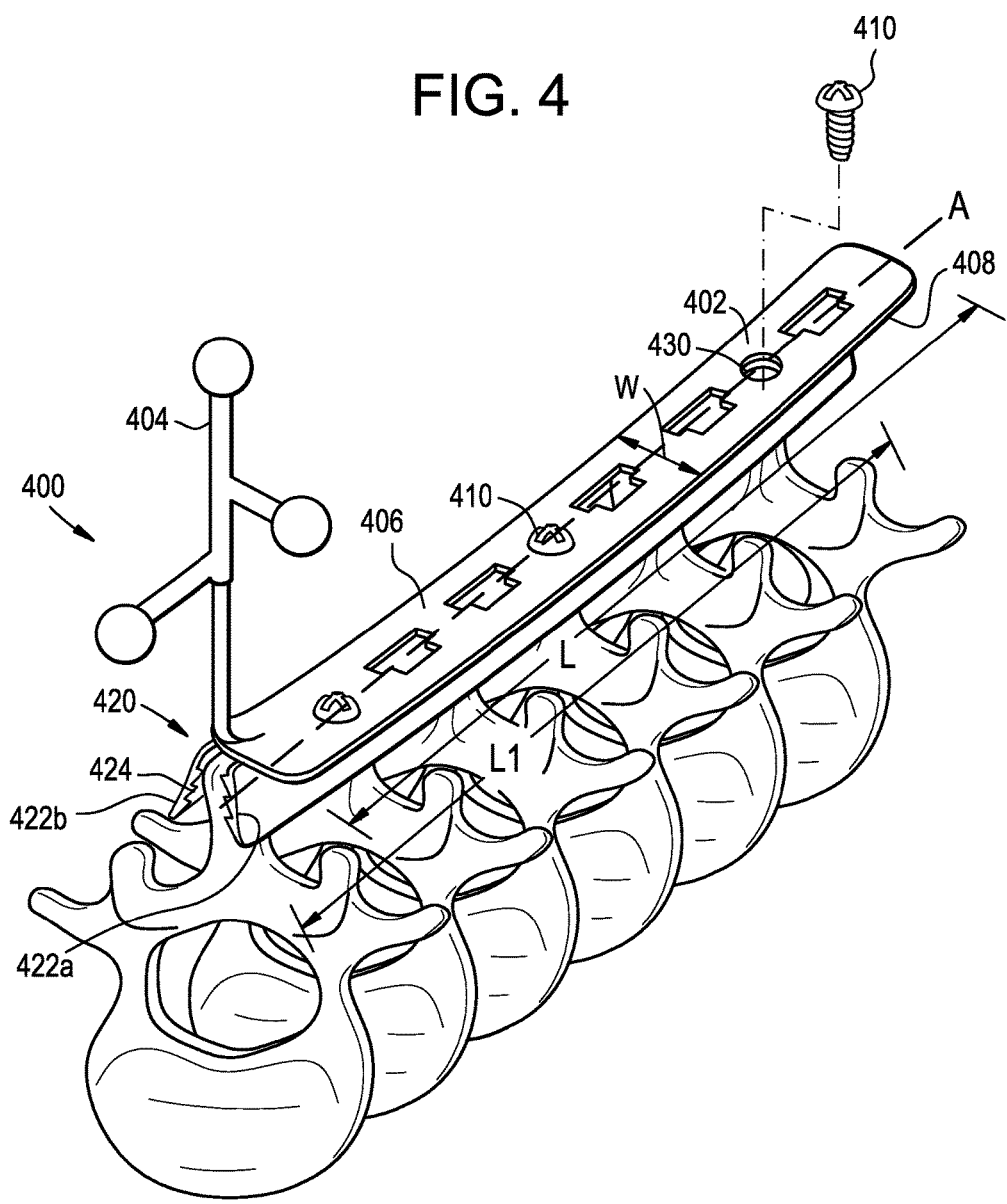
FIG. 4 is a perspective view of an en bloc registration and tracking system attached to a vertebral column, the system having a bridge with a hinged jaw portion that clamps the bridge to the vertebral column.

FIG. 4 illustrates a system 400 which can be used, for example, to register and track multiple vertebral levels as a single functional unit for surgical procedures.

As shown, the system 400 can include a bridge 402 configured for attachment to a patient's spine and a navigation marker 404 coupled to or formed integrally with the bridge. The bridge 402 can include a jaw portion 420 configured to clamp the bridge to a plurality of vertebrae, e.g., to the spinous processes of a plurality of vertebrae as shown. The bridge 402 can include a main body having an upper surface 406 and a lower surface 408, with one or more throughholes 430 extending therebetween. The jaw portion 420 can include a first jaw 422a and a second jaw 422b movable towards one another to clamp an anatomical structure of the patient therebetween. The jaws 422a, 422b can be independent of the main body of the bridge 402, or one or both jaws can be formed by the main body of the bridge. In the illustrated embodiment, the first jaw 422a is defined by a plate pivotally coupled to the main body and the second jaw 422b is defined by the main body. The first jaw 422a can be coupled to the main body of the bridge 402 in various ways, e.g., via a living hinge, a pivot pin, or one or more tabs pivotally received within corresponding slots formed in the main body.

The first jaw 422a can be defined by a hinged plate having a longitudinal axis that is substantially parallel to the longitudinal axis of the bridge 402. The jaws 422a, 422b can have substantially the same length L1 as bridge 402, or can be longer or shorter than the bridge 402.

The first and second jaws 422a, 422b can include teeth 424 thereon. The teeth 424 can be configured to engage a bone structure of the patient to secure the system 400 to the bone. It will be appreciated that the teeth 424 can be located on either of the jaws 422a, 422b, both jaws, or neither jaw. The teeth 424 can be located on an inner surface of the jaws 422a, 422b, on an outer surface of the jaws, at either end of the jaws, or along the entire length of the jaws. As shown in FIG. 4, the jaws 422a, 422b can engage a spinous process therebetween, though it will be appreciated that the jaws can similarly engage another bone or non-bone structure of the patient.

In use, one or more screws 410 can be tightened within the throughholes 430 to bear against the first jaw 422a and cause the first jaw 422a to pivot towards the second jaw 422b, thereby clamping an anatomical structure of the patient therebetween. After passing through the lower surface 408 of the bridge 402, the screws 410 can abut and bear against the first jaw 422a to move the first jaw towards the second jaw 422b. Contact between the screw 410 and the first jaw 422a can drive the teeth 424 of the jaw portion 420 into the bone and lock the jaws 422a, 422b to the bone. In the illustrated embodiment, the screws 410 abut the first jaw 422a while the second jaw 422b remains stationary. It will be appreciated that the throughholes 430 can alternatively be positioned along the bridge 402 such that screws 410 inserted therethrough can abut the second jaw 422b while the first jaw 422a remains stationary. It will also be appreciated that screws 410 can abut both jaws 422a, 422b so as to pivot the jaws 422a, 422b relative to the main body of the bridge 402 to lock the jaws to the bone.

Figure 5A:
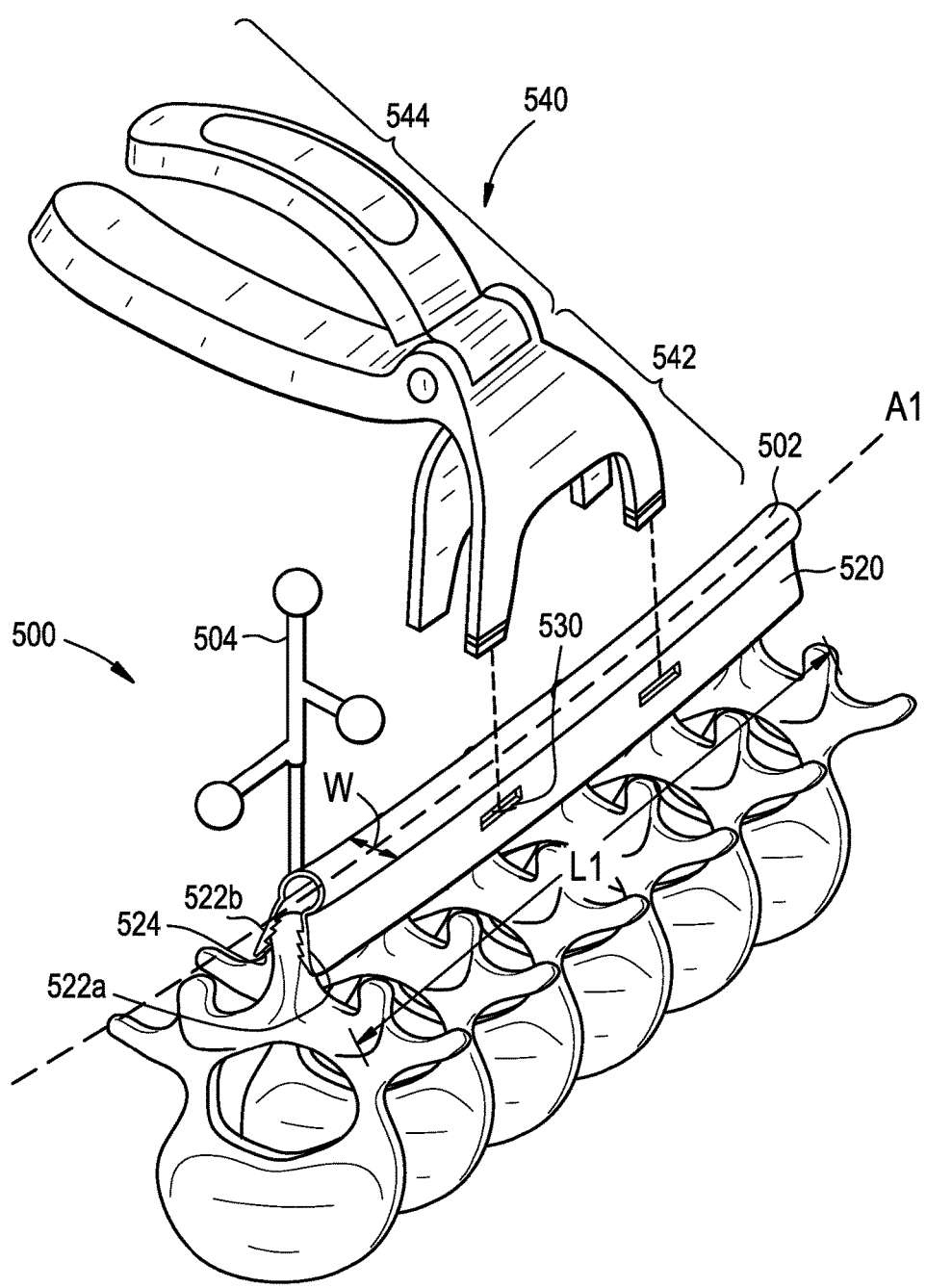
FIG. 5A is a perspective view of an en bloc registration and tracking system attached to a vertebral column and a clamping tool for manipulating the system, the system having a bridge with a spring-biased jaw portion that clamps the bridge to the vertebral column.

FIG. 5 illustrates a system 500 which can be used, for example, to register and track multiple vertebral levels as a single functional unit for surgical procedures.

As shown, system 500 can include a bridge 502 configured for attachment to a patient's spine and a navigation marker 504 coupled to or formed integrally with the bridge. The bridge 502 can include a jaw portion 520 configured to clamp the bridge to a plurality of vertebrae, e.g., to the spinous processes of a plurality of vertebrae as shown. The jaw portion 520 can include a first jaw 522a and a second jaw 522b movable towards one another to clamp an anatomical structure of the patient therebetween. The jaws 522a, 522b can be biased towards one another, e.g., via resilient material properties of the material used to form the bridge 502, or via a bias element such as a leaf spring, coil spring, or the like. The jaws 522a, 522b can include one or more throughholes 530 formed therein to facilitate actuation of the jaws with a clamping tool 540, as described further below. In the illustrated embodiment, the throughholes 530 are defined by a plurality of slots formed in an exterior surface of the jaw portion 520 that can be configured to receive a clamping tool 540 therein. The throughholes 530 can be formed on the first jaw 522a, on the second jaw 522b, or on both jaws.

Figure 5B:
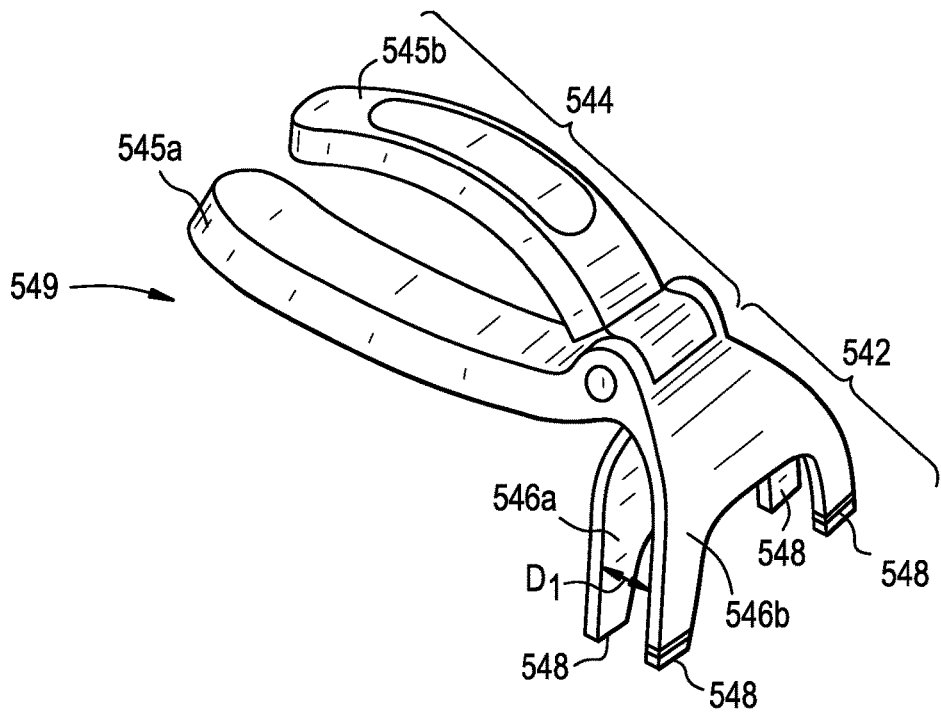
FIG. 5B is a perspective view of the clamping tool of FIG. 5A.

FIG. 5B illustrates an exemplary clamping tool 540 that can be used with the system 500 to open and/or close the jaws 522a, 522b. The clamping tool 540 can include a head portion 542 and a handle portion 544. The head portion 542 can engage the jaws 522a, 522b to secure the system 500 to the vertebral column. The head portion 542 can include two arms 546a, 546b that are movably coupled to one another such that a distance D1 between the arms can be adjusted.

Each arm 546a, 546b can include one or more fingers 548 that protrude distally therefrom. In the illustrated embodiment, two fingers 548 protrude from each arm 546a, 546b, though it will be appreciated that one, or three or more fingers can protrude therefrom. The fingers 548 can be configured to exert a force onto the jaw portion 520 to spread the jaws 522a, 522b apart or to urge the jaws 522a, 522b towards one another. The fingers 548 can be shaped so as to be received within the throughholes 530. A groove or recess can be formed in each finger 548 to help retain the finger within the throughholes 530.

As shown, the handle 544 of the clamping tool can translate a force that a user exerts thereon to move the arms 546a, 546b relative to one another. It will be appreciated that the head portion 542 can be rotatably coupled, pivotably coupled, or hingedly attached to the handle portion 544 of the clamping tool 540. The handle portion 544 can include grasping surfaces 545a, 545b that are configured to be moved by a user to activate the clamping tool 540. In the illustrated embodiment, the handle 544 includes two grasping surfaces 545a, 545b, though it will be appreciated that any number of grasping surfaces can be used.

In use, the clamping tool 540 can be prepared by adjusting the distance D1 between the arms 546a, 546b to be larger than the width of the jaw portion 520. The clamping tool 540 can then be positioned around the jaw portion 520 such that the arms 546a, 546b receive the jaw portion 520 therebetween and the fingers 548 are received within the throughholes 530. A force can be exerted onto the grasping surfaces 545a, 545b of the handle 544 to move the grasping surfaces 545a, 545b toward one another. This movement of the grasping surfaces 545a, 545b can cause the arms 546a, 546b to move toward one another to firmly squeeze the jaws 522a, 522b of the bridge 502 into engagement with an anatomical structure of the patient positioned therebetween, thereby securing the bridge 502 to the patient. Once the system 500 is attached to the patient, the grasping surfaces 545a, 545b can be moved away from one another to release the clamping tool 540 from the system 500, while the jaw portion 520 remains attached to the patient. To remove the jaw portion 520, a force can be applied to the grasping surfaces 545a, 545b to move them apart, which can loosen the attachment between the jaw portion 520 and the vertebral column. It will be appreciated that, in some embodiments, the clamping tool 540 can be instead used to spread the jaws 522a, 522b apart against a biasing force of the jaw portion 520 to allow an anatomical structure of the patient to be positioned between the jaws. The clamping tool 540 can then be released to allow the bias force of the bridge 502 to urge the jaws 522a, 522b towards one another to clamp the patient anatomy therebetween.

Figure 6:
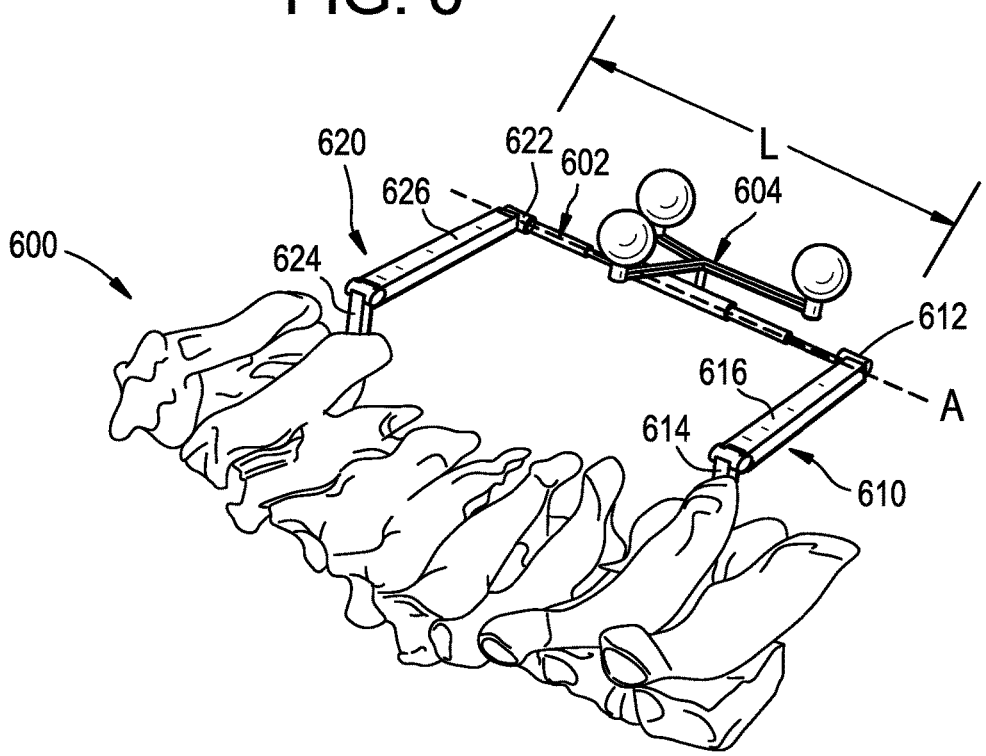
FIG. 6 is a perspective view of an en bloc registration and tracking system attached to a vertebral column, the system having a telescoping bridge and hinged arms for attaching the bridge to the vertebral column.

FIG. 6 illustrates a system 600 which can be used, for example, to register and track multiple vertebral levels as a single functional unit for surgical procedures.

As shown, the system 600 can include a bridge 602 configured for attachment to a patient's spine and a navigation marker 604 coupled to or formed integrally with the bridge. The bridge 602 can have an adjustable length L. For example, the bridge 602 can include a telescoping portion for adjusting the length L of the bridge. The telescoping portion can be formed from concentric rods of varying diameters that are configured to collapse into one another or extend from one another to adjust the length L of the bridge 602. In the illustrated embodiment, the rods at the ends of the bridge 602 can have the smallest diameter, with intermediate rods having diameters of increasing size. It will be appreciated that the rods can be cylindrical, square, oval, circular, triangular, and so forth. As another example, the bridge 602 can include first and second elongate portions slidably coupled to one another to adjust a length L of the bridge and a locking element such as a screw, bolt, etc. configured to secure the first and second portions at a fixed position relative to one another to lock the length L of the bridge 602. The bridge 602 can be offset from the vertebral column such that no portion of the bridge 602 abuts the vertebral column, or at least a portion of the bridge can abut the vertebral column.

The bridge 602 can be adjustable in one or more degrees of freedom with respect to the spinal column when the bridge is attached thereto. For example, as shown, the bridge 602 can be attached to the vertebral column by first and second arms 610, 620 having respective hinges 614. The hinges 614 can allow the bridge 602 to orbit a pivot axis defined by the hinges 614. The pivot axis can be parallel or substantially parallel to the midline of the patient's spine as shown. The ability to pivot the arms 610, 620 can allow the bridge 602 to be positioned in varying orientations relative to the functional unit, which can increase access to the surgical site while maintaining a navigation reference frame.

The arms 610, 620 can be anchored to the posterior aspects of the spine, e.g., using bone anchors, screws, or clamps that are implanted in the pedicle, lateral mass, or lamina of each vertebra, or in the lateral or anterior aspects of the spine. The arms can be anchored to the vertebra such that they are substantially perpendicular to the spinal cord, though it will be appreciated that other orientations are possible, e.g., parallel, angled, and so forth. Multiple systems 600 can be used to register and track vertebral levels as a single functional unit for surgical procedures, e.g., a pair of systems on opposite sides of the spinal cord.

Figure 7:
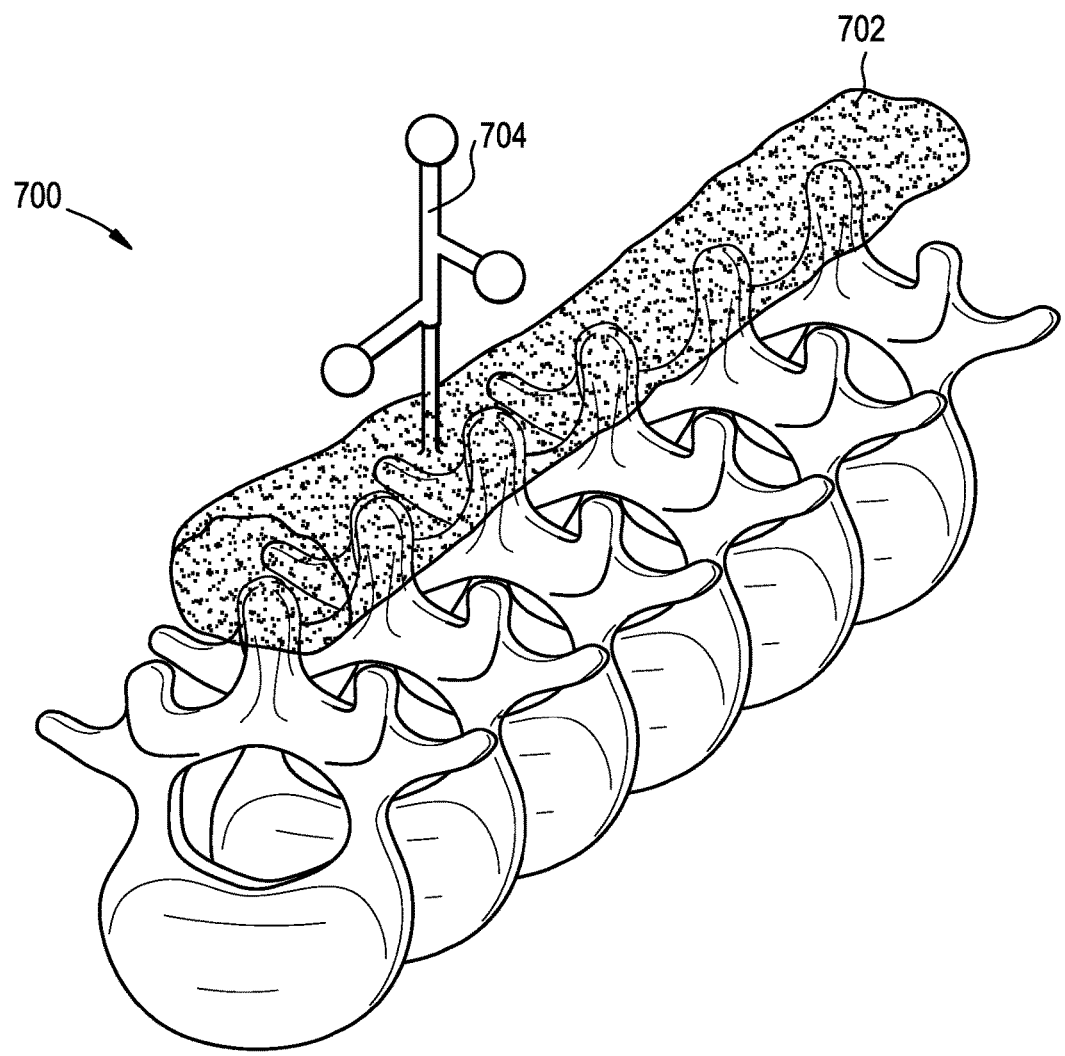
FIG. 7 is a perspective view of an en bloc registration and tracking system attached to a vertebral column, the system having a bridge formed by a mass of bone cement or other material to which a navigation marker is attached.

FIG. 7 illustrates a system 700 which can be used, for example, to register and track multiple vertebral levels as a single functional unit for surgical procedures.

As shown, the system 700 can include a bridge 702 configured for attachment to a patient's spine and a navigation marker 704 coupled to or formed integrally with the bridge. The bridge 702 can be formed at least in part from a mass of curable material attached to a plurality of vertebrae of the patient. For example, the bridge 702 can be formed from a mass of bone cement adhered to the spinous processes of multiple vertebrae of the patient and to the navigation marker 704. Any of a variety of flowable and/or curable materials can be used, including cement, adhesives, glues, composites, thermoplastics, fiberglass, hardenable sterile tape, etc. The material used to form the bridge 702 need not necessarily be curable. For example, high viscosity materials or other moldable or conformable materials can be used to form a bridge that sticks to and stabilizes a plurality of vertebrae. The bridge 702 can be reinforced with wires, mesh, fabric, or an internal frame. In some embodiments, a flexible metallic or polymer mesh can be wrapped around or otherwise conformed to a plurality of vertebrae of the patient. A flowable and curable material can thereafter be applied to the mesh and allowed to cure to form a bridge 702 that attaches and stabilizes a plurality of vertebrae. The navigation marker 704 can be embedded in the curable material as it cures to secure the marker to the bridge 702. As a procedure is nearing completion, or at any other desired time, the bridge 702 can be removed from the patient, for example using a saw, rasp, or other instrument. The mass of curable material can be adhered to the patient, and/or can include one or more screws or other anchors inserted therethrough or extending therearound to attach the material to the patient.

In use, systems of the type described herein can be used to track multiple anatomical structures of a patient, e.g., multiple vertebrae, as a single functional unit. Access to the relevant anatomy of the patient can be obtained using known techniques, including minimally-invasive, open, and hybrid approaches. A system, e.g., of the type described above with respect to FIGS. 1-7, can then be attached to anatomical structure of the patient. For example, referring to FIG. 1, the system 100 can be coupled to the vertebral column of a patient such that the first and second arms 110, 120 extend from first and second respective vertebral levels. Once the system is attached according to the methods described above, the position of the bridge 102 can be registered with the navigation system 101 using the marker 104. The navigation system 101 can determine the position and/or orientation of the marker 104 within the operative field using known techniques. The geometry of the system 100 can be known to the navigation system and can be registered with one or more patient images to allow the position and/or orientation of various anatomical structures of the patient to be determined or estimated from the detected position and/or orientation of the marker 104. This information can be used to guide the user in performing various steps of a surgical procedure. For example, the marker 104 can provide a navigation landmark for guiding insertion of pedicle screws, lateral mass screws, or other bone anchors. By tracking a plurality of vertebrae as a single functional unit, the number of markers required for the surgery and the complexity of the navigation system is reduced. By stabilizing and/or immobilizing a plurality of vertebrae using the system 100, relative movement between the individual vertebrae of the unit can be limited or prevented, allowing for accurate navigation based off of one or more markers 104 that are common to the plurality of vertebrae. This can also obviate the need to re-register individual vertebrae with the navigation system 101 due to movement of the vertebrae during the procedure. By knowing the location of the extents of a given spinal segment (as defined by the attached bridge), an accurate approximation of the intermediate vertebrae and nearby structures can be obtained using the navigation system 101. When tracking is no longer required or desired by the user, the system 100 can be removed from the patient.

In one or more of the examples illustrated herein, the systems connect the spinous processes of six vertebrae, e.g., C2, C3, C4, C5, C6, and C7, en bloc for registration during navigation assisted surgery. It will be appreciated that this arrangement is merely exemplary, and that any number of systems can be used at any level of the spine. Also, it will be appreciated that the system can attach to shorter or longer ranges of vertebrae, e.g., C3-C5, C2-T2, T1-T12, and so forth. The bridge can attach to each vertebral level in a spinal segment or can skip levels within the segment. For example, the bridge 102 can include two arms 110, 120 connected to a pair of end vertebrae in a spinal segment, though it will be appreciated that the bridge can include a fewer or greater number of arms that can attach to each vertebral level in the spinal segment. In some embodiments, the arms can be omitted and the bridge 102 can abut one or more vertebrae directly.

While devices and methods for registering and tracking multiple vertebral levels as a single functional unit for surgical procedures are disclosed herein, the disclosed systems can be used to register and track other anatomical structures of the patient, including bones or bone fragments, non-bone structures, etc. or non-anatomical structures, such as implants or surgical instruments. Any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The various components of the systems disclosed herein can be rigid or flexible. One or more components or portions of the systems can be formed from a radiopaque material to facilitate visualization under fluoroscopy and other imaging techniques, or from a radiolucent material so as not to interfere with visualization of other structures. Exemplary radiolucent materials include carbon fiber and high-strength polymers. The various components of the systems disclosed herein can be formed from any of a variety of materials suitable for use in surgical applications, including metals such as titanium, titanium alloys, or stainless steel, polymers such as PEEK, ceramics, fibers such as carbon fiber, and combinations thereof. Other exemplary materials include curable materials, such as a glues, adhesives, cements, composites, thermoplastics, fiberglass, hardenable sterile tape, etc. The curable material can be reinforced with a fabric or mesh.

The systems and methods disclosed herein can be used in minimally-invasive surgery and/or open surgery. The systems disclosed herein can be fully or partially implanted, or can be used externally to the patient. While the systems and methods disclosed herein are generally described in the context of the spine, it will be appreciated that the systems and methods disclosed herein can be used with any human or animal bone or other tissue, in any of a variety of surgeries performed on humans or animals, and/or in fields unrelated to implants or surgery.

Although specific embodiments are described above, it should be understood that numerous changes may be made within the spirit and scope of the concepts described.

The invention claimed is:

1. A surgical navigation method, comprising:
   attaching a plurality of vertebrae of a patient to one another using a bridge, the bridge limiting or preventing relative movement between the plurality of vertebrae, the plurality of vertebrae defining a single functional unit once connected to the bridge, the bridge having a navigation marker;
   using a surgical navigation system, guiding movement of a navigated object relative to a constituent member of the functional unit based on the navigation marker; and
   adjusting a position and/or orientation of the bridge relative to the plurality of vertebrae by pivoting the bridge about one or more jointed arms of the bridge that are attached to one or more of the plurality of vertebrae.

2. The method of claim 1, wherein the navigation marker of the bridge and a navigation marker of the navigated object are the only navigation markers used in guiding movement of the object.

3. The method of claim 1, wherein the navigated object comprises at least one of a bone anchor and a surgical instrument.

4. The method of claim 1, wherein said movement comprises driving the navigated object into the constituent member of the functional unit.

5. The method of claim 1, wherein the constituent member comprises one of the plurality of vertebrae to which the bridge is attached or a vertebra disposed between the plurality of vertebrae.

6. The method of claim 1, wherein the bridge limits or prevents relative movement between the plurality of vertebrae and any vertebrae disposed between the plurality of vertebrae.

7. The method of claim 1, further comprising determining a position and orientation of the navigated object relative to a constituent member of the functional unit.

8. The method of claim 1, further comprising any of collapsing one or more of a plurality of concentric rods into one another or extending one or more of the plurality of concentric rods from one another to adjust a length of the bridge based on a length of the functional unit.

9. The method of claim 1, wherein attaching the plurality of vertebrae comprises attaching the spinous processes of the plurality of vertebrae to the bridge.

10. The method of claim 1, wherein the bridge pivots about a pivot axis defined by one or more hinges of the jointed arms.

11. The method of claim 10, wherein the pivot axis is substantially parallel to a midline of the plurality of vertebrae.

12. A surgical navigation method, comprising:
   attaching spinous processes of a plurality of vertebrae of a patient to one another using a bridge, the bridge immobilizing the plurality of vertebrae relative to one another and having a navigation marker attached thereto;
   registering or tracking the plurality of vertebrae as a single functional unit using the navigation marker; and
   any of collapsing one or more of a plurality of concentric rods into one another or extending one or more of the plurality of concentric rods from one another to adjust a length of the bridge based on a length of the functional unit.

13. A surgical device, comprising:
   a bridge having a first end and a second end, the bridge having a length between the first and second ends sufficient to span multiple vertebrae of a patient;
   a securement device configured to attach the bridge to a plurality of vertebrae to connect and immobilize the vertebrae; and
   a navigation marker formed on or coupled to the bridge;
   wherein the securement device comprises first and second arms extending from the bridge, the arms including at least one joint to allow the bridge to pivot about the arms to adjust a position or orientation thereof.

14. The device of claim 13, further comprising a surgical navigation system configured to track the plurality of vertebrae as a single functional unit using the navigation marker.

15. The device of claim 13, wherein the securement device comprises first and second jaws configured to clamp onto a plurality of vertebrae.

16. The device of claim 15, wherein the securement device comprises a screw configured to be tightened to force the first and second jaws towards one another.

17. The device of claim 13, wherein the securement device comprises a curable material.

18. The device of claim 13, wherein the bridge includes a plurality of concentric rods; and
   wherein a length of the bridge is adjustable by any of collapsing one or more of the plurality of concentric rods into one another or extending one or more of the plurality of concentric rods from one another.

19. The device of claim 13, wherein the length of the bridge is adjustable by a telescoping portion of the bridge.

* * * * *